United States Patent
Hashimoto et al.

(10) Patent No.: US 6,384,386 B2
(45) Date of Patent: May 7, 2002

(54) HEATER CONTROL APPARATUS FOR EXHAUST GAS SENSOR

(75) Inventors: Kohji Hashimoto; Katsuya Nakamoto, both of Tokyo (JP)

(73) Assignee: Mitsubishi Denki Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/759,341

(22) Filed: Jan. 16, 2001

(30) Foreign Application Priority Data

Jul. 3, 2000 (JP) ........................................ 2000-200526

(51) Int. Cl.[7] ............................................... H05B 1/02
(52) U.S. Cl. ..................... 219/497; 219/202; 219/481; 219/205; 219/508; 123/697
(58) Field of Search ................................ 219/497, 501, 219/508, 509, 481, 202–206, 490; 123/689, 697

(56) References Cited

U.S. PATENT DOCUMENTS

| 4,504,732 A | * | 3/1985 | Bube et al. ............... 219/497 |
| 5,285,762 A | * | 2/1994 | Werner et al. ............ 123/60 |
| 5,288,974 A | * | 2/1994 | Hanzic ..................... 219/501 |
| 5,740,675 A | * | 4/1998 | Shimasaki et al. ......... 60/274 |
| 5,816,231 A | * | 10/1998 | Inoue ...................... 123/689 |

FOREIGN PATENT DOCUMENTS

| JP | 1-172746 | 7/1989 |
| JP | 7-119736 | 12/1995 |
| JP | 8-313476 | 11/1996 |
| JP | 9-292364 | 11/1997 |

* cited by examiner

Primary Examiner—Mark Paschall
(74) Attorney, Agent, or Firm—Sughrue Mion, PLLC (57) ABSTRACT

The heater control apparatus comprises an exhaust gas sensor 6 for detecting an oxygen concentration in exhaust gases of an internal combustion engine, a heater 5 for heating this exhaust gas sensor 6 to a predetermined temperature, a power source including a battery 2 for supplying electric power to this heater 5 and a charging generator 4 for charging this battery 2, a switching element 19 inserted into a circuit for supplying electric power to the heater 5 from the power source, control means 12 for performing current-carrying control of the switching element 19 so as to maintain a temperature of the exhaust gas sensor 6 at a predetermined value, and an overvoltage detection element 28 for outputting an abnormal detection signal when a voltage of the power source exceeds a predetermined value, and it is constructed so that the switching element 19 is broken to stop the passage of current to the heater 5 by the abnormal detection signal of the overvoltage detection element 28 when a voltage of the charging generator 4 abnormally increases due to disconnection etc. of the battery 2 of the power source.

8 Claims, 5 Drawing Sheets

HEATER CONTROL APPARATUS FOR EXHAUST GAS SENSOR

BACKGROUND OF THE INVENTION

1. Field of the Invention

This invention relates to a heater control apparatus for oxygen concentration sensor heating for detecting an oxygen concentration contained in exhaust gases of an internal combustion engine.

2. Description of the Related Art

A technique for making purification of the exhaust gases and improvements in fuel consumption by detecting the oxygen concentration contained in the exhaust gases of the internal combustion engine and performing feedback control on an air-fuel ratio of an air-fuel mixture supplied to the internal combustion engine in response to the detected oxygen concentration is well known, and the technique is widely used in the internal combustion engine for vehicle. An exhaust gas sensor for detecting the oxygen concentration needs to stabilize detection characteristics of the oxygen concentration by maintaining a temperature at an activation region and for this purpose, a heater control apparatus for passing a current through a heater built into the sensor and controlling a passage current to hold a temperature of the sensor at a predetermined value is used and various techniques are disclosed as this control method.

For example, a technique for detecting a resistance value of a heater from voltage and current values of the heater and calculating a temperature of the heater from this resistance value to see an activation state of an exhaust gas sensor and also performing duty control of a passage current for temperature control and speeding up activation by continuous passage of current at the time of low temperature (for example, at the time of starting of an internal combustion engine) is disclosed in JP-A-8-313476. Also, a technique for detecting a resistance value of an exhaust gas sensor itself with high accuracy to detect the temperature and also switching a voltage applied to the exhaust gas sensor at the time of detecting an oxygen concentration to a voltage for resistance detection at a predetermined time constant in order to reduce this detection time and detecting an internal resistance value of the exhaust gas sensor from a change state of voltage and current at that time is disclosed in JP-A-9-292364.

Further, a technique in which when temperature control of an exhaust gas sensor is performed by turning on or off a heater, stabilization of an element temperature of the exhaust gas sensor and accuracy of air-fuel ratio control are improved while increasing a life of the heater by providing delay time in on-off control and operating the delay time using a running state of an internal combustion engine (for example, rotational speed) as parameters to reduce the number of on-off actions of the heater is disclosed in JP-A-7-119736. Furthermore, a technique for holding accuracy of a heater temperature and improving durability and detection accuracy of an oxygen concentration by setting a desired value of a heater resistance in response to power consumption of a heater and an exhaust gas flow and controlling an applied voltage so that a resistance value of the heater becomes equal to this desired value is disclosed in JP-A-1-172746.

As indicated in each the conventional example, the variety of techniques for speeding up the activation at the time of starting while controlling the temperature to improve the durability and the detection accuracy of the oxygen concentration by performing current-carrying control to the heater are disclosed, but a power source for heating the heater of the exhaust gas sensor used in a vehicle is a battery mounted in the vehicle and a change in voltage of this battery is large during operation of the vehicle, so that it takes time to perform initial heating at the time of a low voltage and if case of improving a heating capability in order to cope with this, burning of the heater or driving elements was caused at the time of a high voltage or troubles could not be avoided in temperature control by the conventional current-carrying control. Particularly, in case that a state of connection between the battery and a charging generator for charging this battery became worse, a voltage of the charging generator might increase transiently and a relatively high voltage from this charging generator might be applied to the heater and in such a case, the burning troubles of the heater or the driving elements could not be avoided.

SUMMARY OF THE INVENTION

The invention is implemented to solve such problems, and it is an object of the invention to obtain a compact and cheap heater control apparatus for exhaust gas sensor in which troubles such as burning do not occur at the time of overvoltage even in case of using a heater with high heating capability and a sufficient preventive safety measures are taken.

A heater control apparatus for exhaust gas sensor according to the invention comprises an exhaust gas sensor which is provided in an exhaust passageway of an internal combustion engine and detects an oxygen concentration in exhaust gases, a heater for heating this exhaust gas sensor to a predetermined temperature, a power source including a battery for supplying heating electric power to this heater and a charging generator for charging this battery, a switching element inserted into a circuit for supplying electric power to the heater from this power source, control means including a microcomputer for performing current-carrying control of the switching element so as to maintain a temperature of the exhaust gas sensor at a predetermined value, and an overvoltage detection element for outputting an abnormal detection signal when a voltage of the power source exceeds a predetermined value, and it is constructed so that the switching element is interrupted to stop the passage of current to the heater by the abnormal detection signal of the overvoltage detection element when a voltage of the charging generator abnormally increases due to disconnection etc. of the battery of the power source.

Also, the heater control apparatus comprises an exhaust gas sensor which is provided in an exhaust passageway of an internal combustion engine and detects an oxygen concentration in exhaust gases, a heater for heating this exhaust gas sensor to a predetermined temperature, a power source including a battery for supplying heating electric power to this heater and a charging generator for charging this battery, a switching element inserted into a circuit for supplying electric power to the heater from this power source, control means including a microcomputer for performing current-carrying control of the switching element so as to maintain a temperature of the exhaust gas sensor at a predetermined value, circuit abnormal detection means for detecting circuit abnormality such as short-circuit troubles of a current carrying circuit to the heater and outputting an abnormal detection signal, an overvoltage detection element for outputting an abnormal detection signal when a voltage of the charging generator increases and exceeds a predetermined value due to disconnection etc. of the battery of the power source, and a second switching element which is inserted into a circuit for supplying electric power to the heater from this power source and responds to the abnormal detection signal of the circuit abnormal detection means and also responds to the abnormal detection signal of the overvoltage detection element and interrupts a current flowing through the heater.

Further, the control means performs current-carrying control of the switching element at a switching ratio in response to a value of a source voltage.

Furthermore, a gate element for driving the switching element for interrupting a current flowing through the heater by the abnormal detection signal is provided and the abnormal detection signal is applied to the gate element directly without passing the control means and the switching element is constructed so as to interrupt the current by operations of the gate element.

Moreover, the heater control apparatus further comprises storage means for encoding and storing signal contents of the abnormal detection signal when the overvoltage detection element or the circuit abnormal detection means outputs the abnormal detection signal, and display means for displaying the fact that the abnormal detection signal has been outputted.

In addition, the control means measures an internal resistance value before start of a run and an internal resistance value during the run of the exhaust gas sensor and calculates a temperature of the exhaust gas sensor from a ratio between both of the resistance values.

Also, the control means reads a voltage value across both ends of the switching element at opening of the switching element and a current value flowing through the switching element at closing in a time division manner and calculates a resistance value of the heater from the voltage value and the current value and calculates a temperature of the exhaust gas sensor as a function of this resistance value of the heater.

DETAILED DESCRIPTION OF THE PRESENT INVENTION

First Embodiment

Figure 1:
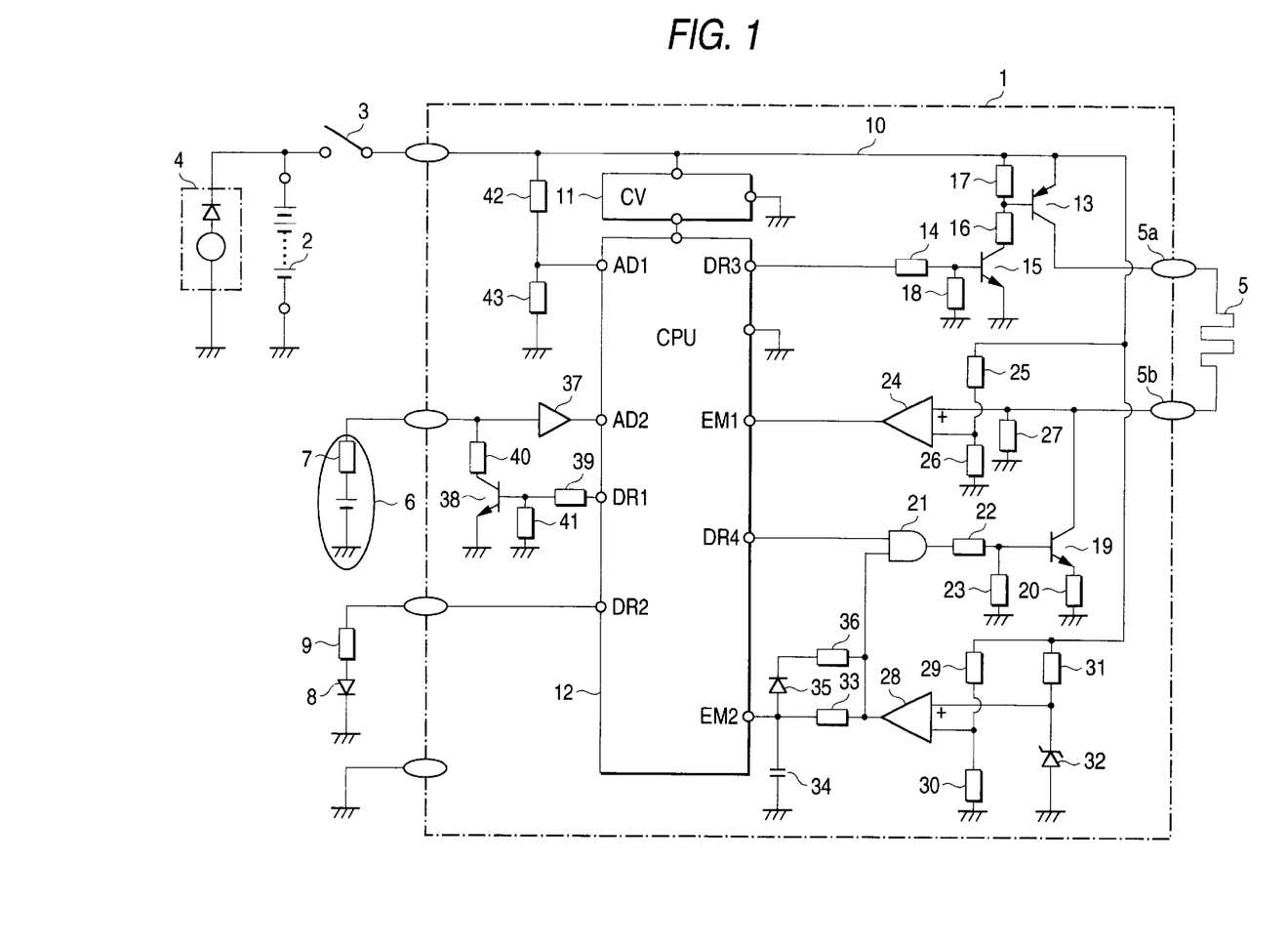
FIG. 1 is a circuit diagram of a heater control apparatus for exhaust gas sensor according to a first embodiment of the invention.
Figure 2:
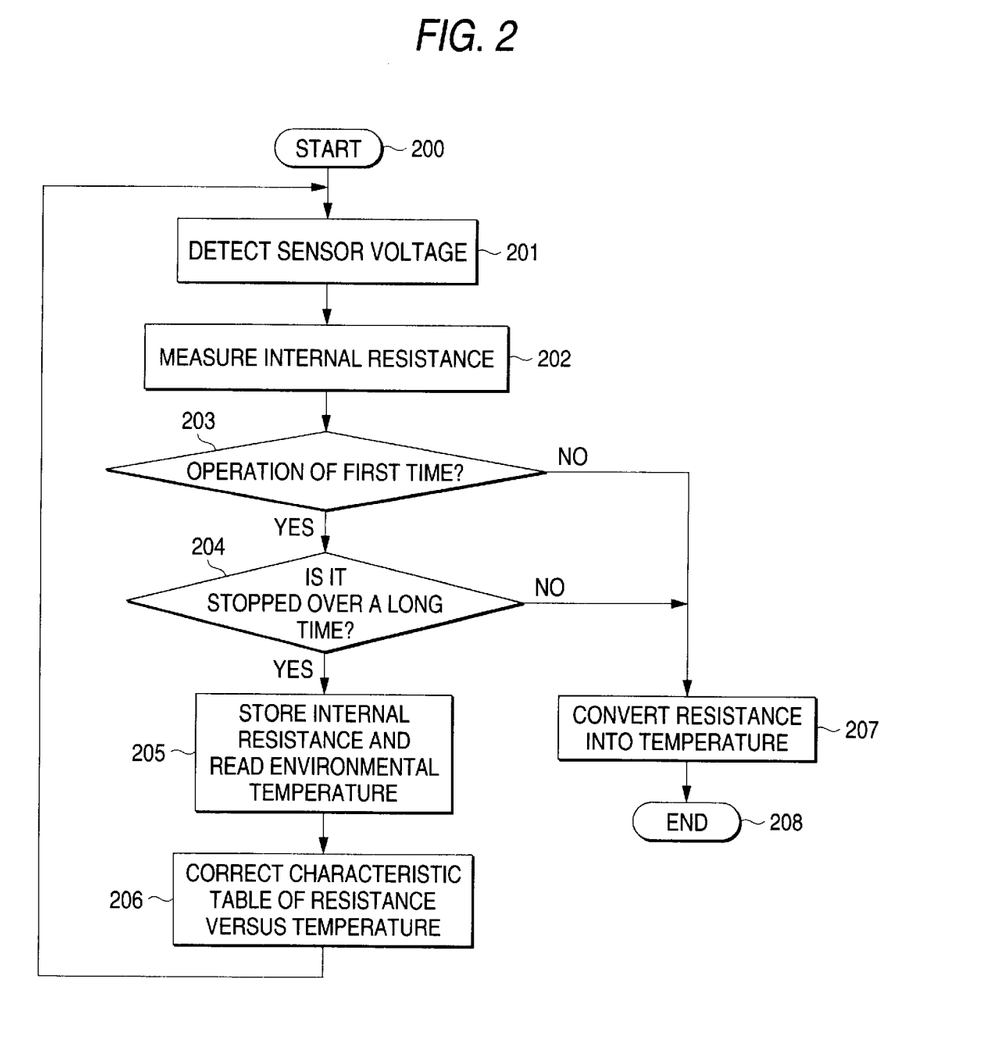
FIG. 2 is a flowchart illustrating operations of the heater control apparatus for exhaust gas sensor according to the first embodiment of the invention.
Figure 3:
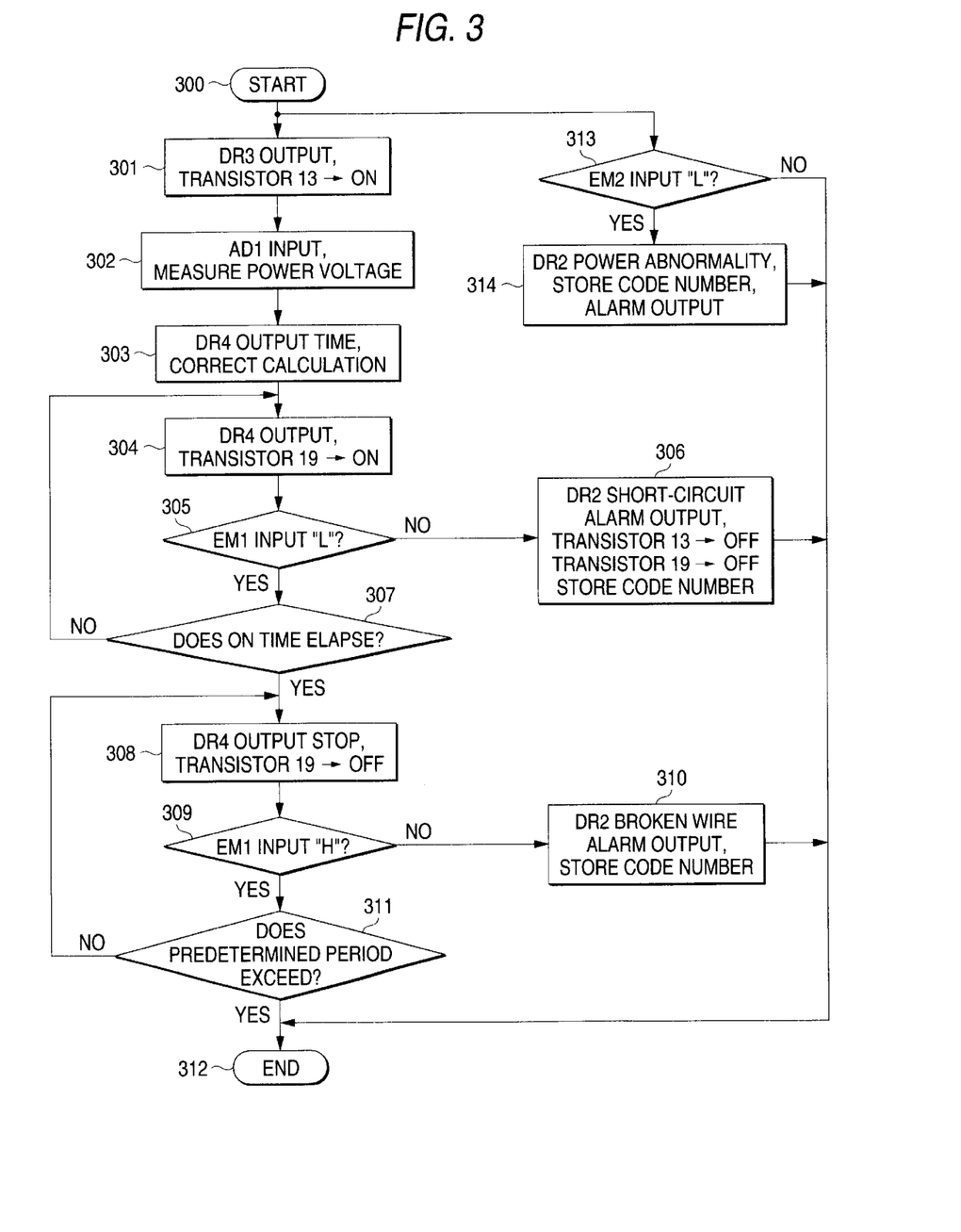
FIG. 3 is a flowchart illustrating operations of the heater control apparatus for exhaust gas sensor according to the first embodiment of the invention.

FIG. 1 is a circuit diagram of a heater control apparatus for exhaust gas sensor according to a first embodiment of the invention, and FIGS. 2 and 3 are flowcharts illustrating the operations. In FIG. 1, numeral 1 is a heater control apparatus, and numeral 2 is a battery for supplying electric power to the heater control apparatus 1 through a key switch 3, and numeral 4 is a charging generator for vehicle mounting for charging the battery 2, and numeral 5 is a heater controlled by the heater control apparatus 1, and numeral 6 is an exhaust gas sensor having an internal resistor 7 while being constructed so as to be integrated or closely placed with the heater 5 to be heated, and numeral 8 is a light emitting diode acting as display means driven by the heater control apparatus 1 through a resistor 9.

Numeral 10 is a power line within the heater control apparatus 1, and numeral 11 is a constant-voltage power source for supplying a constant voltage (for example, DC 5 V) to a microprocessor (hereinafter called "CPU") 12 acting as control means, and numeral 13 is a transistor constructing a second switching element connected to one terminal 5a of the heater 5 from the power line 10 and the second switching element 13 is driven through a resistor 14 and a transistor 15 from an output terminal DR3 of the CPU 12 and it is constructed so as to turn on the second switching element 13 by turning on the transistor 15. Numeral 16 is a resistor for connecting a collector of the transistor 15 to a base of the second switching element 13, and numeral 17 is a ballast resistor for making connection between the base and an emitter of the second switching element 13, and numeral 18 is a ballast resistor for making connection between a base and an emitter of the transistor 15.

Numeral 19 is a transistor connected between the other terminal 5b of the heater 5 and a current detection resistor 20 and acting as a first switching element for performing on-off control of the passage of current to the heater 5, and the first switching element 19 is constructed so as to be driven through a gate element 21 and a resistor 22 from an output terminal DR4 of the CPU 12. Further, numeral 23 is a ballast resistor connected to a base of the first switching element 19. Also, numeral 24 is a circuit abnormal detection element for dividing a voltage from the power line 10 by resistors 25 and 26 to input the voltage to a minus terminal and inputting a voltage of a pull-down resistor 27 connected to the other terminal 5b of the heater 5 and a voltage of the current detection resistor 20 to a plus terminal, and the output is inputted to an input terminal EM1 of the CPU 12.

Numeral 28 is an overvoltage detection element for dividing the voltage from the power line 10 by resistors 29 and 30 to input the voltage to a minus terminal and inputting a voltage of a constant-voltage diode 32 connected through a resistor 31 from the power line 10 to a plus terminal, and the output terminal is connected to one input terminal of the gate element 21 and also is connected to an input terminal EM2 of the CPU 12 through a high resistor 33. Also, a capacitor 34 is connected to this terminal EM2, and it is constructed so that the capacitor 34 is charged through the high resistor 33 when the overvoltage detection element 28 is at an H level and when it is changed into an L level, the capacitor 34 is discharged through a discharge path formed by a series connection of a diode 35 and a low resistor 36 connected in parallel with the high resistor 33.

Also, numeral 37 is an amplifier which amplifies an output voltage of the exhaust gas sensor 6 and inputs the voltage to an input terminal AD2 for A/D conversion of the CPU 12. A transistor 38 is driven through a resistor 39 by a signal voltage from an output terminal DR1 of the CPU 12 and connects a load resistor 40 to the exhaust gas sensor 6. Numeral 41 is a ballast resistor connected between a base and an emitter of the transistor 38. Numerals 42 and 43 are voltage dividing resistors which divide a power voltage supplied from the battery 2 and input the voltage to an input terminal AD1 for A/D conversion of the CPU 12. Also, the light emitting diode 8 is driven through the resistor 9 by a signal from an output terminal DR2 of the CPU 12.

In the heater control apparatus for exhaust gas sensor according to the first embodiment of the invention constructed in this manner, the CPU 12 operates as shown in the flowcharts of FIGS. 2 and 3. In FIG. 2, when an operation is started in step 200, in step 201, the CPU 12 turns off the transistor 38 for a predetermined time by a signal of the output terminal DR1 and takes a no-load output voltage of the exhaust gas sensor 6 in the input terminal AD2 of the CPU 12 through the amplifier 37. An input voltage of this AD2 is a voltage corresponding to an oxygen concentration contained in exhaust gases.

Subsequently, in step 202, the transistor 38 is turned on for a predetermined time by the signal of the output terminal DR1, and an on-load output voltage divided by the internal resistor 7 of the exhaust gas sensor 6 and the load resistor 40 is taken in the input terminal AD2 through the amplifier 37 and a resistance value of the internal resistor 7 is calculated. Here, when a no-load output voltage of the exhaust gas sensor 6 in step 201 is E0 and an on-load output voltage of the exhaust gas sensor 6 in step 202 is E1 and a resistance value of the load resistor 40 is R1 and a resistance value of the internal resistor 7 of the exhaust gas sensor 6 is R0, a relationship of E1=E0×R1/(R1+R0) is obtained and R0 is calculated. Incidentally,this value of R0 changes as an exponential function of the reciprocal of an absolute temperature of the exhaust gas sensor 6 and varies according to variations between products of the exhaust gas sensor 6 or a change with time.

Next, in step 203, it is determined whether an operation of this routine is the first time or not. If it is determined that the operation is the first time in this step, an operation proceeds to step 204 and here, it is determined whether an internal combustion engine is stopped over a long time and a temperature of the exhaust gas sensor 6 decreases to an outside-air temperature or not in comparison with an outside-air temperature sensor (not shown). If it is determined that the temperature of the exhaust gas sensor 6 decreases to the outside-air temperature in step 204, an operation proceeds to step 205, and the resistance value R0 of the internal resistor 7 obtained in step 202 is stored and the outside-air temperature by the outside-air temperature sensor is read and stored. When processing in step 205 is completed, an operation proceeds to step 206 and here, a table of the internal resistor versus temperature is created by the resistance value R0 of the internal resistor 7 and the outside-air temperature, and the operation returns to step 201 and this routine is repeated.

Since it is determined that operations of the second time or later is not the operation of the first time in step 203, an operation proceeds from step 203 to step 207. Also, if it is determined that there is not the stop time enough to decrease the temperature of the exhaust gas sensor 6 in step 204, an operation proceeds to step 207 and here, the present temperature of the exhaust gas sensor 6 is calculated from the latest information of the resistance value R0 of the internal resistor 7 obtained in step 202 and the table of the internal resistor versus temperature created in step 206. When this temperature is calculated, an operation proceeds to step 208 and the routine is ended, and by returning to step 201 again from this and repeating the routine from step 201 to step 208 at a predetermined time interval, the temperature of the exhaust gas sensor 6 at the present time is always calculated and this value is given to step 303 of FIG. 3 described below.

In operations of FIG. 3, when an operation is first started in step 300, the CPU 12 turns on the transistor 15 by a signal of the output terminal DR3 in step 301and thereby, the transistor 13 which is the second switching element is brought into conduction and then in step 302, a power voltage is measured from a signal inputted to the input terminal AD1 of the CPU 12. Next, an operation proceeds to step 303 and a current-carrying on-off time ratio to the heater 5, so-called a duty ratio is calculated and determined from the temperature of the exhaust gas sensor 6 at the present time obtained in step 207 and the power voltage obtained in step 302. Here, the duty is set to a higher value with a decrease in the temperature of the exhaust gas sensor 6 at the present time or with a decrease in the power voltage, and a reduction in heating time is made. Further, in step 304, a signal is outputted from the DR4 of the CPU 12 by this calculated current-carrying on time width, and the transistor 19 which is the first switching element is brought into conduction through the gate element 21.

In the above steps, the first switching element 19 and the second switching element 13 are brought into conduction and thereby, a current is passed through the heater 5 and a voltage is generated across both ends of the current detection resistor 20. Step 305 is a step in which the input terminal EM1 of the CPU 12 inputs a signal from the circuit abnormal detection element 24 to make a determination, and when a voltage of the current detection resistor 20 becomes too large due to short-circuit troubles of the heater 5 or external wiring, a plus terminal voltage of the circuit abnormal detection element 24 becomes large and an output of the circuit abnormal detection element 24, namely an input to the terminal EM1 becomes an H level to make a determination of NO in step 305, and when a current value is normal due to no short-circuit troubles, the plus terminal voltage of the circuit abnormal detection element 24 is small and the input to the terminal EM1 becomes an L level to make a determination of YES in step 305.

If the determination in step 305 is NO, namely an overcurrent is detected, an operation proceeds to step 306, and outputs of the DR3 and DR4 of the CPU 12 are stopped and the first switching element 19 and the second switching element 13 become in an OFF state and the passage of current through the heater 5 is stopped and also, a signal is outputted from the terminal DR2 and the light emitting diode 8 operates and an abnormal alarm is given. Here, even when either the first switching element 19 or the second switching element 13 is in a short-circuit breakage state due to the overcurrent, the passage of current can be stopped by an operation of the other switching element and double safety measures are taken and further in this step, a code number corresponding to the abnormal state is stored in storage means of the CPU 12 and an abnormal cause can be read out as necessary.

If the determination in step 305 is YES, an operation proceeds to step 307, and is determined whether the current-carrying on time width set in step 303 elapses or not and if not, an operation returns to step 304 and the routine to step 307 is repeated. If the predetermined on time elapses in step 307, an operation proceeds to step 308 and a signal of the DR4 of the CPU 12 is stopped to turn off the first switching element 19. When the first switching element 19 is turned off, a voltage of the pull-down resistor 27 receiving the power voltage is applied to the plus terminal voltage of the circuit abnormal detection element 24, and while an output voltage becomes an H level for normal, an output voltage of the circuit abnormal detection element 24 becomes an L level for abnormal (for example, a broken wire or poor contact in the heater 5 or an external circuit).

Step 309 determines this state and for abnormal, in step 310, while a signal is outputted from the terminal DR2 of the CPU 12 and the light emitting diode 8 operates and an abnormal alarm is given, a code number corresponding to the broken wire trouble is stored and an abnormal cause can be read out as necessary. In this manner, the circuit abnormal detection element 24 has abnormal monitor functions of both of on and off times of the first switching element 19. In step 311, it is determined whether the total on and off time of duty control of the first switching element 19 calculated in step 303 elapses or not and if not, the routine from step 308 is repeated, and if so, an operation returns from step 312 to step 300 and enters the next routine.

Step 313 is a periodical interruption routine and determines logical levels of the input terminal EM2 of the CPU 12. A voltage of a plus input terminal of the overvoltage detection element 28 is set to a voltage higher than the voltage in which the voltage of the constant-voltage diode 32 is divided by the voltage dividing resistors 29 and 30, and an output of the overvoltage detection element 28 is in an H level under normal conditions. In case that looseness occurs in terminals of the battery 2, the charging generator 4 becomes a light load, so that a generated voltage abnormally increases during transient time necessary for voltage control. When such an overvoltage is applied to the heater control apparatus 1 or the heater 5, a divided voltage by the voltage dividing resistors 29 and 30 becomes higher than the voltage of the constant-voltage diode 32 and an input of the terminal EM2 changes to an L level and in step 314, the first switching element 19 and the second switching element 13 become in an OFF state immediately by signals of the DR3 and the DR4, with the result that a passage of overcurrent through the heater 5, the first switching element 19 and the second switching element 13 is prevented. Also, other than this routine, an output of the overvoltage detection element 28 is applied to the gate element 21 and the first switching element 19 is immediately interrupted without time delay to protect a circuit.

In the capacitor 34 connected to the terminal EM2, a charging circuit is formed by the high resistor 33 and a discharging circuit is formed by the low resistor 36, so that a voltage immediately decreases when a logical level of the overvoltage detection element 28 changes from H to L and it takes a predetermined time to increase the voltage when the logical level changes from L to H, and the passage of current is stopped even in response to abnormality of a short time and a predetermined time constant is provided for recovery time and thereby, safety is maintained. Further, in this logical determination, after turning on the power, the predetermined time is released and a malfunction at the time of turning on the power is prevented. Also, when an overvoltage abnormality is detected in step 313, in step 314, a signal is outputted from the terminal DR2 and the light emitting diode 8 operates and a code number corresponding to the abnormal state is stored.

Second Embodiment

Figure 4:
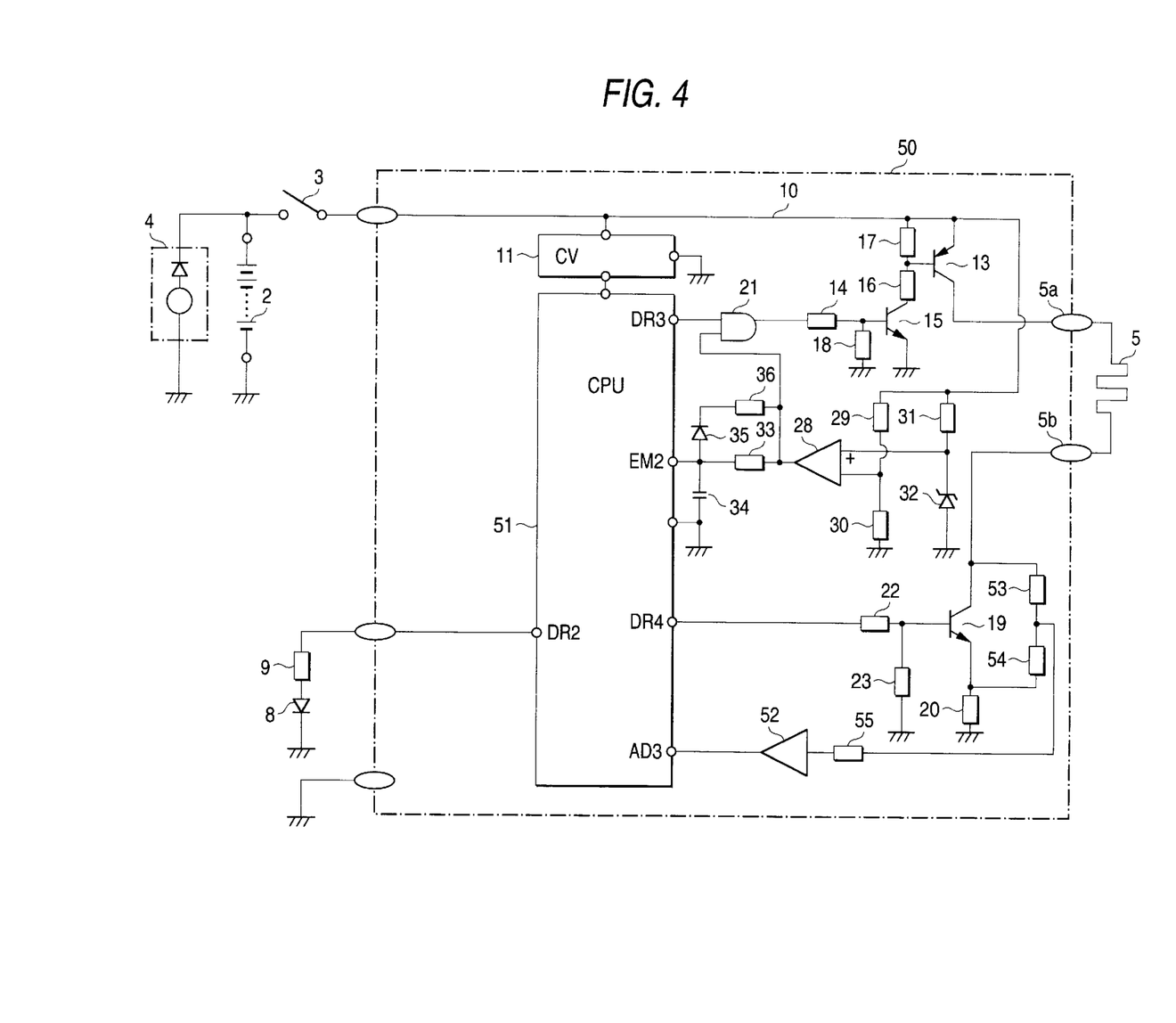
FIG. 4 is a circuit diagram of a heater control apparatus for exhaust gas sensor according to a second embodiment of the invention.
Figure 5:
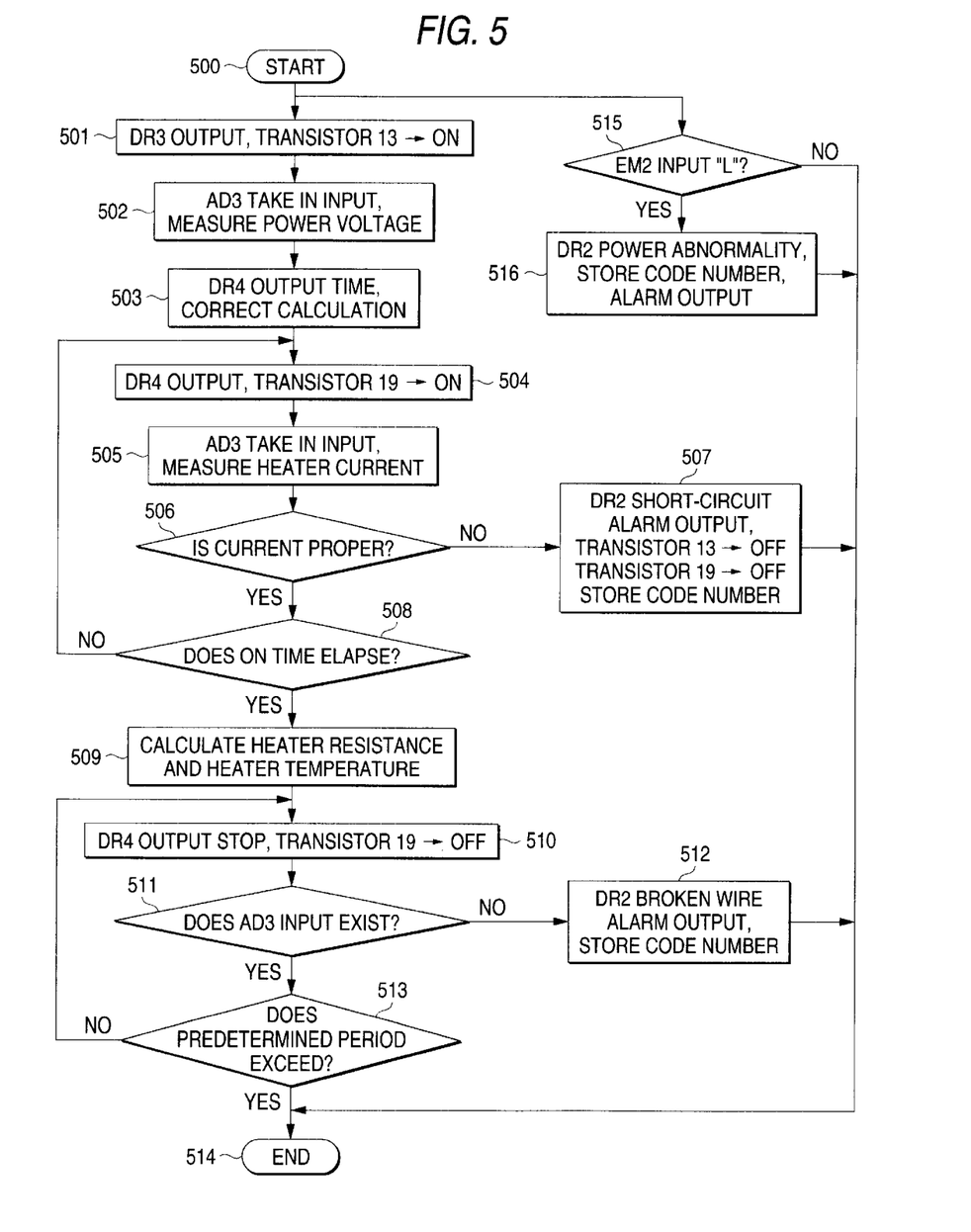
FIG. 5 is a flowchart illustrating operations of the heater control apparatus for exhaust gas sensor according to the second embodiment of the invention.

FIG. 4 is a circuit diagram of a heater control apparatus for exhaust gas sensor according to a second embodiment of the invention, and FIG. 5 is a flowchart illustrating the operations, and like reference characters are given to the same parts as the first embodiment. In FIG. 4, numeral 50 is a heater control apparatus, and numeral 2 is a battery for supplying electric power to the heater control apparatus 50 through a key switch 3, and numeral 4 is a charging generator for vehicle mounting for charging the battery 2, and numeral 5 is a heater controlled by the heater control apparatus 50 and the heater 5 is integrated or closely placed with an exhaust gas sensor (not shown in FIG. 4). Numeral 8 is a light emitting diode acting as display means driven by the heater control apparatus 50 through a resistor 9.

Numeral 10 is a power line within the heater control apparatus 50, and numeral 11 is a constant-voltage power source for supplying a constant voltage (for example, DC 5 V) to a CPU 51, and numeral 13 is a transistor constructing a second switching element connected to one terminal 5a of the heater 5 from the power line 10 and in this embodiment, the second switching element 13 is driven through a gate element 21, a resistor 14 and a transistor 15 from an output terminal DR3 of the CPU 51 and it is constructed so as to turn on the second switching element 13 through a resistor 16 by turning on the transistor 15. Also, numerals 17 and 18 are ballast resistors.

Numeral 19 is a transistor connected between the other terminal 5b of the heater 5 and a current detection resistor 20 and forming a first switching element for performing on-off control of the passage of current to the heater 5 and in this embodiment, the first switching element 19 is constructed so as to be driven through a resistor 22 from an output terminal DR4 of the CPU 51. Further, numeral 23 is a ballast resistor. Numeral 28 is an overvoltage detection element for dividing a voltage from the power line 10 by resistors 29 and 30 to input the voltage to a minus terminal and inputting a voltage of a constant-voltage diode 32 connected through a resistor 31 from the power line 10 to a plus terminal, and the output is connected to one input terminal of the gate element 21 and also is connected to an input terminal EM2 of the CPU 51 through a high resistor 33. Also, a capacitor 34 is connected to the terminal EM2, and it is constructed so that the capacitor 34 is charged through the high resistor 33 when the overvoltage detection element 28 is at an H level and when it is changed into an L level, the capacitor 34 is discharged through a discharge path formed by a series connection of a diode 35 and a low resistor 36 connected in parallel with the high resistor 33.

Numeral 52 is an amplifier which is inputted through a resistor 55 from an intermediate connection point between voltage dividing resistors 53 and 54 connected between a collector and an emitter of the transistor 19 forming the first switching element and gives an output to an input terminal AD3 for A/D conversion of the CPU 51, and the voltage dividing resistors 53 and 54 are selected so that the resistor 53 has a value sufficiently larger than a resistance value of the heater. 5 and a ratio of a value of the resistor 53 to a value of the resistor 54 is substantially equal to a ratio of the resistance value of the heater 5 to a resistance value of the current detection resistor 20. Also, as described below, by them, circuit abnormal detection means of a current-carrying circuit to the heater 5 is also constructed.

In the heater control apparatus for exhaust gas sensor according to the second embodiment of the invention constructed in this manner, the CPU 51 operates as shown in the flowchart of FIG. 5. When an operation is first started in step 500, the CPU 51 turns on the transistor 15 through the gate element 21 by a signal of the output terminal DR3 in step 501 and thereby, the transistor 13 which is the second switching element is brought into conduction. Then, in step 502, a power voltage is measured from a signal inputted to the input terminal AD3 of the CPU 51. In measurement of this power voltage, a voltage proportional to the power voltage is applied to the intermediate connection point between the voltage dividing resistors 53 and 54 in the case that the second switching element 13 is turned on and the first switching element 19 is in an off state, and the measurement is obtained by inputting this voltage to the terminal AD3 through the amplifier 52.

Subsequently, in step 503, a current-carrying on-off time ratio to the heater 5 is calculated from the power voltage obtained in step 502 and a temperature of the heater 5 obtained in step 509 described later and in a manner similar to the first embodiment, a current-carrying duty ratio to the heater 5 is also determined from a temperature of the exhaust gas sensor and a value of the power voltage. Further, in step 504, a signal is outputted from the DR4 of the CPU 51 by this calculated current-carrying on time width, and the transistor 19 which is the first switching element is brought into conduction through the resistor 22. In the above steps, the first switching element 19 and the second switching element 13 are brought into conduction and thereby, a current is passed through the heater 5 and a voltage is generated across both ends of the current detection resistor 20. In step 505, this voltage across both ends of the current detection resistor 20 is obtained from the intermediate connection point between the voltage dividing resistors 53 and 54, and a value of the current passed through the heater 5 is measured by taking the voltage in the input terminal AD3 of the CPU 51 through the amplifier 52.

Next, an operation proceeds to step 506 and it is determined whether the current of the heater 5 obtained in step 505 is proper or not. Here, if the current of the heater 5 increases due to short-circuit troubles of the heater 5 or an external circuit and the voltage of the current detection resistor 20 is larger than a predetermined value, it is determined that there is not the proper current and an operation proceeds to step 507, and if it is determined that there is the proper current, an operation proceeds to step 508. In step 507, outputs of the DR3 and DR4 of the CPU 51 are stopped and the first switching element 19 and the second switching element 13 are turned off and the current of the heater 5 is interrupted and also, a signal is outputted from the terminal DR2 and the light emitting diode 8 is operated and an abnormal alarm is given. Here, even when either the first switching element 19 or the second switching element 13 is in a short-circuit breakage state, the passage of current can be stopped by an operation of the other switching element and double safety measures are taken and further in this step, a code number corresponding to the abnormal state is stored in storage means of the CPU 51 and an abnormal cause can be read out as necessary.

Also, If the current value is proper, an operation proceeds to step 508 and it is determined whether the current-carrying on time width set in step 503 elapses or not, and an operation returns to step 504 and the routine to step 508 is repeated until this time width elapses. If it is determined that the predetermined time width elapses, an operation proceeds to step 509, and a resistance value of the heater 5 is calculated from the power voltage obtained in step 502 and the current value obtained in step 505, and a temperature of the heater 5 at the present time is calculated by a characteristic table of the resistance value versus temperature of the heater 5 stored previously and also, a temperature of the exhaust gas sensor is calculated from this temperature of the heater 5 based on a predetermined function. Then, since the predetermined on time width has elapsed, in step 510, an output of the terminal DR4 of the CPU 51 is stopped to turn off the first switching element 19.

Subsequently, an operation proceeds to step 511 and it is determined whether a signal from the amplifier 52 exists in the input terminal AD3 of the CPU 51 or not. In case that broken wire troubles occur in the heater 5 or external wire, a voltage is not generated at the intermediate connection point between the voltage dividing resistors 53 and 54 even in the off state of the first switching element 19, so that a signal is not inputted to the input terminal AD3 and if this signal is not inputted, an operation proceeds to step 512, and a signal is outputted from the terminal DR2 and the light emitting diode 8 is operated to output a broken wire alarm and also, a code number corresponding to the broken wire trouble is stored and an abnormal cause can be read out as necessary. In this manner, a signal input from the amplifier 52 to the input terminal AD3 of the CPU 51 has abnormal monitor functions of both of on and off times of the first switching element 19, and also serves as circuit abnormal detection means.

If the signal from the amplifier 52 exists in step 511, an operation proceeds to step 513 and here, it is determined whether the total on and off time of duty control to the first switching element 19 calculated in step 503 elapses or not and if not, an operation returns from step 513 to step 510 and the routine is repeated, and if so, an operation returns from step 514 to step 500 and enters the next routine.

Step 515 is a periodical interruption routine and determines logical levels of the input terminal EM2 of the CPU 51. A voltage of the constant-voltage diode 32 inputted to a plus input terminal of the overvoltage detection element 28 is set to a voltage higher than the voltage by the voltage dividing resistors 29 and 30 inputted to a minus input terminal, and an output of the overvoltage detection element 28 is in an H level under normal conditions. In a manner similar to the case of the first embodiment, when looseness occurs in terminals of the battery 2, a generated voltage of the charging generator 4 abnormally increases during transient time and an abnormal voltage is applied to the heater control apparatus 50 or the heater 5, but in such a case, a voltage by the voltage dividing resistors 29 and 30 becomes higher than the voltage of the constant-voltage diode 32, so that an input of the terminal EM2 changes to an L level and this L level is detected and in step 516, the first switching element 19 and the second switching element 13 are turned off immediately by a signal stop of the DR3 and the DR4, with the result that a passage of overcurrent through the heater 5, the first switching element 19 and the second switching element 13 is prevented. Also, in a manner similar to the case of the first embodiment, other than this routine, an output of the overvoltage detection element 28 is applied to the gate element 21, and it is constructed so that the second switching element 13 is immediately shut off without time delay to protect a circuit.

Also, the operations to the capacitor 34 connected to the terminal EM2 of the CPU 51 are similar to that of the first embodiment, and a charging path is formed by the high resistor 33 and a discharging path is formed by the low resistor 36, so that a voltage immediately decreases when a logical level of the overvoltage detection element 28 changes from H to L and it takes a predetermined time to increase the voltage when the logical level changes from L to H, and the passage of current is stopped even in response to abnormality of a short time and a predetermined time constant is provided for recovery time and thereby, safety is maintained. Also, in this logical determination, after turning on the power, the predetermined time is released and a malfunction at the time of turning on the power is prevented, and when an overvoltage abnormality is detected in step 515, in step 516, a signal is outputted from the terminal DR2 and the light emitting diode 8 operates and a code number corresponding to the abnormal state is stored.

Incidentally, in the heater control apparatus for exhaust gas sensor of the first and second embodiments indicated above, though a temperature of the exhaust gas sensor 6 or its vicinity is detected and feedback control is performed so that the temperature of the exhaust gas sensor 6 becomes a predetermined value, for example, the CPU may be programmed so as to perform heating control according to a running state of an internal combustion engine so that after starting of the internal combustion engine, for a period during which an output of the exhaust gas sensor reaches a predetermined value, the heater is heated with 100% of the passage of current in a low temperature state of cooling water and the heater is heated with a duty ratio of 30% during a light load run and the cooling water with the temperature higher than or equal to the predetermined value and the heating is stopped during high load of the internal combustion engine. Also, though a bipolar transistor is used in the first and second switching elements, a MOS transistor having drain, source and gate may be used.

According to a heater control apparatus for exhaust gas sensor of the invention as described above, the heater control apparatus comprises an exhaust gas sensor provided in an exhaust passageway of an internal combustion engine, a power source including a battery for passing a current through a heater for heating the exhaust gas sensor and a charging generator for charging this battery, a switching element connected in series with a circuit for supplying electric power to the heater from the power source, control means for performing current-carrying control of the switching element at a switching ratio in response to a temperature of the exhaust gas sensor, and an overvoltage detection element for interrupting the switching element to stop the passage of current to the heater by detecting a voltage of the power source when the voltage of the power source exceeds a predetermined value, and it is constructed so that the switching element is speedily interrupted by an output of the overvoltage detection element when an overvoltage is applied to the heater due to disconnection etc. of the battery, so that the heater control apparatus in which the heater is surely protected and the heater can be used with the maximum capability under normal conditions and troubles such as burning do not occur and the heater with high heating capability can be used to speed activation of the exhaust gas sensor can be obtained.

Also, a second switching element and circuit abnormal detection means for detecting a broken wire or a short circuit of a power supply circuit are provided in a circuit for supplying electric power to the heater from the power source and this second switching element is constructed so as to interrupt speedily by an output of the overvoltage detection element or an output of the circuit abnormal detection means, so that a interruption of the power supply circuit due to an overcurrent of short-circuit troubles can be surely prevented in addition to the effects described above. Further, since it is constructed so that current-carrying control of the switching element for passing a current through the heater for heating the exhaust gas sensor is performed at a switching ratio in response to a source voltage and a temperature of the exhaust gas sensor is maintained at a predetermined value, the exhaust gas sensor can be speedily made in an active state even under low temperature or low voltage, and for overvoltage or circuit abnormality, storage means for storing abnormal contents and display means for displaying this contents are added, so that the contents of troubles can be speedily grasped to take speedy measures.

Also, it is constructed so as to calculate a temperature of the exhaust gas sensor from internal resistance values of the exhaust gas sensor at the time of start of a run and during the run, so that temperature control with high accuracy can be performed, and further it is constructed so as to read detection of a voltage and detection of a current during on-off operations of the switching element in a time division manner and calculate a temperature of the heater from the current and the voltage, temperature control can be performed by a small amount of hardware configurations and simple means and the control apparatus can be miniaturized, with the result that the excellent heater control apparatus for exhaust gas sensor can be obtained.

What is claimed is:

1. A heater control apparatus comprising:

an exhaust gas sensor provided in an exhaust passageway of an internal combustion engine, the exhaust gas sensor for detecting an oxygen concentration in exhaust gases;

a heater for heating the exhaust gas sensor to a predetermined temperature;

a power source including:
  a battery for supplying heating electric power to the heater; and
  a charging generator for charging the battery, a switching element inserted into a circuit for supplying electric power to the heater from the power source;

a controller including a microcomputer for performing current-carrying control of the switching element to maintain a temperature of the exhaust gas sensor at a predetermined value; and an overvoltage detection element for outputting an abnormal detection signal when a voltage of the power source exceeds a predetermined value, wherein the switching element is interrupted to stop the passage of current to the heater by the abnormal detection signal of the overvoltage detection element when a voltage of the charging generator abnormally increases due to disconnection of the battery of the power source.

2. The heater control apparatus as defined in claim 1, wherein the controller performs current-carrying control of the switching element at a switching ratio in response to a value of a source voltage.

3. The heater control apparatus as defined in claim 1, further comprising a gate element for driving the switching element for interrupting a current flowing through the heater by the abnormal detection signal, wherein the abnormal detection signal is applied to the gate element directly the switching element is constructed to interrupt the current by operations of the gate element.

4. The heater control apparatus as defined in claim 1, the heater control apparatus further comprising:

a storage unit for encoding and storing signal contents of the abnormal detection signal when the overvoltage detection element or the circuit abnormal detector outputs the abnormal detection signal; and a display unit for displaying that the abnormal detection signal has been outputted.

5. The heater control apparatus as defined in claim 1, wherein the controller measures an internal resistance value before start of a run and an internal resistance value during the run of the exhaust gas sensor, calculates a temperature of the exhaust gas sensor from a ratio between both of the resistance values and performs current-carrying control of the switching element at a switching ratio in response to the temperature.

6. The heater control apparatus as defined in claim 1, wherein the controller reads a voltage value across both ends of the switching element at opening of the switching element and a current value flowing through the switching element at closing in a time division manner, calculates a resistance value of the heater from the voltage value and the current value, calculates a temperature of the exhaust gas sensor as a function of this resistance value of the heater, and performs current-carrying control of the switching element at a switching ratio in response to this temperature of the sensor.

7. A heater control apparatus comprising:
- an exhaust gas sensor provided in an exhaust passageway of an internal combustion engine, the exhaust gas sensor for detecting an oxygen concentration in exhaust gases;
- a heater for heating the exhaust gas sensor to a predetermined temperature;
- a power source including:
  - a battery for supplying heating electric power to the heater; and
  - a charging generator for charging this battery;
- a first switching element inserted into a circuit for supplying electric power to the heater from the power source,
- a controller including a microcomputer for performing current-carrying control of the switching element to maintain a temperature of the exhaust gas sensor at a predetermined value;
- a circuit abnormal detector for detecting circuit abnormality and outputting an abnormal detection signal;
- an overvoltage detection element for outputting an abnormal detection signal when a voltage of the charging generator abnormally increases and exceeds a predetermined value due to disconnection of the battery of the power source; and
- a second switching element inserted into a circuit for supplying electric power to the heater from the power source, the second switching element for responding to the abnormal detection signal of the circuit abnormal detector, responding to the abnormal detection signal of the overvoltage detection element, and interrupting a current flowing through the heater.

8. The heater control apparatus as defined in claim 7, wherein the circuit abnormal detector detects short-circuit troubles of a current-carrying circuit to the heater.

* * * * *